US006565209B2

(12) United States Patent
Campin

(10) Patent No.: US 6,565,209 B2
(45) Date of Patent: May 20, 2003

(54) RANGE-EXTENDING SYSTEM AND SPATIAL FILTER FOR ENHANCING HARTMANN-SHACK IMAGES AND ASSOCIATED METHODS

(75) Inventor: John Alfred Campin, Orlando, FL (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/993,065

(22) Filed: Nov. 13, 2001

(65) Prior Publication Data

US 2002/0118340 A1 Aug. 29, 2002

Related U.S. Application Data

(63) Continuation-in-part of application No. 09/842,264, filed on Apr. 25, 2001.
(60) Provisional application No. 60/199,562, filed on Apr. 25, 2000.

(51) Int. Cl.[7] .................................................. A61B 3/10
(52) U.S. Cl. ..................................................... 351/212
(58) Field of Search ................................ 351/211, 212, 351/214, 221, 246; 356/121, 124

(56) References Cited

U.S. PATENT DOCUMENTS

| | | | |
|---|---|---|---|
| 4,725,138 A | | 2/1988 | Wirth et al. |
| 4,750,818 A | | 6/1988 | Cochran |
| 5,221,834 A | | 6/1993 | Lisson et al. |
| 5,684,545 A | | 11/1997 | Dou et al. |
| 5,822,035 A | | 10/1998 | Bille |
| 5,825,476 A | | 10/1998 | Abitol et al. |
| 5,841,511 A | | 11/1998 | D'Souza et al. |
| 6,047,091 A | | 4/2000 | Anderson |
| 6,299,311 B1 | * | 10/2001 | Williams et al. ............. 351/221 |
| 6,497,483 B2 | * | 12/2002 | Frey et al. ................... 351/212 |

FOREIGN PATENT DOCUMENTS

| | | |
|---|---|---|
| WO | WO 99/27334 | 6/1999 |
| WO | WO 00/10448 | 3/2000 |
| WO | 00/19885 | 4/2000 |

OTHER PUBLICATIONS

Wallner, Edward P., "Comparison of Wavefront Sensor Configurations Using Optimal Reconstruction and Correction," San Diego, Aug. 25, 1982, Proceedings of SPIE, vol. 351, pps. 42–53.

Hamam, H., "A Direct Technique for Calculating the Profile of Aberration of the Eye Measured by a Modified Hartmann–Shack Apparatus," *Optics Communications 173*, Oct. 1999, pp. 23–26.

Liang, et al., "Aberrations and Retinal Image Quality of the Normal Human Eye," *J. Opt. Soc. Am. A*, vol. 14, No. 11, Nov. 1997, pp. 2873–2883.

* cited by examiner

*Primary Examiner*—George Manuel

(57) ABSTRACT

A range of a wavefront sensor is extended by focusing collimated light onto a lenslet array, an output creating a grid formed by edges of the lenslets and a reference spot in the members of the grid. Each reference spot has a known relationship to the grid member and a centroid. A relationship between the reference centroids is determined. Next a wavefront emanating from an eye is focused onto the lenslet array, with the output from the lenslet array forming the grid and aberrated eye spots thereon, each eye spot having a centroid. A relationship between the eye spot centroids is determined. One known relationship between one reference centroid and the centroid of one eye spot is identified. Finally, at least some of the remaining relationships between the reference centroids and the eye spot centroids are determined. The determined relationships provide a measure indicative of the eye aberration.

52 Claims, 11 Drawing Sheets

RANGE-EXTENDING SYSTEM AND SPATIAL FILTER FOR ENHANCING HARTMANN-SHACK IMAGES AND ASSOCIATED METHODS

CROSS-REFERENCE TO RELATED APPLICATION

This application is a continuation-in-part of application Ser. No. 09/842,264, "Spatial Filter for Enhancing Hartmann-Shack Images and Associated Methods," filed Apr. 25, 2001, which itself claims priority from commonly owned provisional application Serial No. 60/199,562, filed Apr. 25, 2000, "Spatial Filtering to Enhance Hartmann-Shack Images." The disclosures of these references is incorporated in their entirety herein.

BACKGROUND OF THE INVENTION

1. Field of the Invention

The present invention relates to systems and methods for performing and analyzing data from objective measurements of a visual system, and, more particularly, to such a system and method for enhancing data from a Hartmann-Shack image and for extending a range of Hartmann-Shack-based wavefront sensors.

2. Description of Related Art

Optical systems having a real image focus can receive collimated light and focus it at a point. Such optical systems can be found in nature, e.g., human and animal eyes, or can be manmade, e.g., laboratory systems, guidance systems, and the like. In either case, aberrations in the optical system can affect the system's performance. By way of example, the human eye will be used to explain this problem.

A perfect or ideal eye diffusely reflects an impinging light beam from its retina through the optics of the eye, which includes a lens and a cornea. For such an ideal eye in a relaxed state, i.e., not accommodating to provide near-field focus, reflected light exits the eye as a sequence of plane waves. However, an eye typically has aberrations that cause deformation or distortion of reflected light waves exiting the eye. An aberrated eye diffusely reflects an impinging light beam from its retina through its lens and cornea as a sequence of distorted wavefronts.

One method of measuring ocular refractive errors is disclosed in U.S. Pat. No. 5,258,791 to Penney et al. for "Spatially Resolved Objective Autorefractometer," which teaches the use of an autorefractometer to measure the refraction of the eye at numerous discrete locations across the corneal surface. Penney '791 further teaches the use of autorefractometer measurements in determining an appropriate corneal surface reshaping to provide emmetropia, a condition of a normal eye when parallel beams or rays of light are focused exactly on the retina and vision is perfect.

By way of example, one method and system known in the art are disclosed by Junzhong Liang et al. in "Objective Measurement of Wave Aberrations of the Human Eye with the Use of a Hartmann-Shack Wave-Front Sensor" [J. Opt. Soc. Am. 11(7), July 1994, pp 1949–57]. Liang et al. teach the use of a Hartmann-Shack wavefront sensor to measure ocular aberrations by measuring the wavefront emerging from the eye by the retinal reflection of a focused laser light spot on the retina's fovea. The actual wavefront is reconstructed using wavefront estimation with Zernike polynomials. A parallel beam of laser light passes through beam splitters and a lens pair, which brings the beam to a focus point on the retina by the optics of the eye. Possible myopia or hyperopia of the tested eye is corrected by movement of a lens within the lens pair. The focused light on the fovea is then assumed to be diffusely reflected and acts as a point source located on the retina. The reflected light passes through the eye and forms a distorted wavefront in front of the eye that results from the ocular aberrations. The aberrated wavefront is then directed to the wavefront sensor.

The Hartmann-Shack wavefront sensor disclosed by Liang et al. includes two identical layers of cylindrical lenses with the layers arranged so that lenses in each layer are perpendicular to one another, as further disclosed in U.S. Pat. No. 5,062,702 to Bille. In this way, the two layers operate as a two-dimensional array of spherical lenslets that divide the incoming light wave into subapertures. The light through each subaperture is brought to focus in the focal plane of the lens array where a charge-coupled-device (CCD) image module resides.

The system of Liang et al. is calibrated by impinging an ideal plane wave of light on the lenslet array so that a reference or calibrating pattern of focus spots is imaged on the CCD. Since the ideal wavefront is planar, each spot related to the ideal wavefront is located on the optical axis of the corresponding lenslet. When a distorted wavefront passes through the lenslet array, the image spots on the CCD are shifted with respect to a reference pattern generated by the ideal wavefront. Each shift is proportional to a local slope, i.e., partial derivatives of the distorted wavefront, which partial derivatives are used to reconstruct the distorted wavefront, by means of modal wavefront estimation using Zernike polynomials.

However, the system disclosed by Liang et al. is effective only for eyes having fairly good vision. Eyes that exhibit considerable myopia (near-sightedness) cause the focus spots to overlap on the CCD, thereby making local slope determination practically impossible for eyes having this condition. Similarly, eyes that exhibit considerable hyperopia (farsightedness) deflect the focus spots such that they do not impinge on the CCD, thereby again making local slope determination practically impossible for eyes having this condition.

Various embodiments of a method and system for objectively measuring aberrations of optical systems by wavefront analysis have been disclosed in commonly owned application Ser. No. 09/566,668, "Apparatus and Method for Objective Measurement and Correction of Optical Systems Using Wavefront Analysis," filed May 8, 2000, which is hereby incorporated by reference herein. In this invention, an energy source generates a beam of radiation. Optics, disposed in the path of the beam, direct the beam through a focusing optical system (e.g., the eye) that has a rear portion (e.g., the retina) that provides a diffuse reflector. The beam is diffusely reflected back from the rear portion as a wavefront of radiation that passes through the focusing optical system to impinge on the optics. The optics project the wavefront to a wavefront analyzer in direct correspondence with the wavefront as it emerges from the focusing optical system. A wavefront analyzer is disposed in the path of the wavefront projected from the optics and calculates distortions of the wavefront as an estimate of ocular aberrations of the focusing optical system. The wavefront analyzer includes a wavefront sensor coupled to a processor that analyzes the sensor data to reconstruct the wavefront to include the distortions thereof.

A perfectly collimated light beam (i.e., a bundle of parallel light rays, here a small-diameter, eye-safe laser beam) incident on a perfect, ideal emmetropic eye, focuses to a diffraction-limited small spot on the retina. This perfect focusing is true for all light rays passing through the entrance pupil, regardless of position. From the wavefront perspective, the collimated light represents a series of perfect plane waves striking the eye. The light emanates from an illuminated spot on the retina as wavefronts exiting as a series of perfect plane waves, which are directed onto a wavefront analyzer for measuring distortions from ideality.

In one embodiment, the radiation is optical radiation and the wavefront sensor is implemented using a plate and a planar array of light-sensitive cells. The plate is generally opaque but has an array of light-transmissive apertures that selectively let impinging light therethrough. The plate is disposed in the path of the wavefront so that portions of the wavefront pass through the light-transmissive apertures. The planar array of cells is arranged parallel to and spaced apart from the plate by a selected distance. Each portion of the wavefront passing through one of the light-transmissive apertures illuminates a geometric shape covering a unique plurality of cells.

The wavefront optical path relays the re-emitted wavefront from the corneal plane to an entrance face of a Hartman-Shack wavefront sensor. The wavefront incident on the sensor is received by a sensitive charged-coupled-device (CCD) camera and an optical plate containing an array of lenslets. The lenslet array is parallel to the CCD detector face, with a distance therebetween approximately equal to the focal length of each lens in the lenslet array. The lenslet array divides the incoming wavefront into a matching array of "wavelets," each of which focuses to a small spot on the CCD detector plane. The constellation of wavelet spots in the CCD is used to reconstruct the shape of the incident wavefront. Collimated light striking the lenslet at normal (perpendicular) incidence would focus to the spot on the CCD face where this optical axis intersects. The optics of the apparatus provides such collimated light to the wavefront sensor using a calibration optical path.

In the case of a reflected aberrated wavefront, light focuses to a spot displaced from the collimated reference point by a distance $D_x$. The distance from the lenslet face to the CCD surface, $D_z$, is precisely known. Therefore, dividing the measured displacement, $D_x$, by the known propagation distance, $D_z$, the slope of the wavefront at the location of this lens element is determined. The same calculation is applied in the y direction within the plane, and the entire process applied to every lenslet element irradiated by the wavefront. A mathematical algorithm is then applied to reconstruct the wavefront shape consistent with the calculated $D_x/D_z$ and $D_y/D_z$ slope data. Regardless of which wavefront sensor is used, the distance between the planar array of cells and the opaque plate, or the array of lenslets, can be varied to adjust the slope measurement gain of the wavefront sensor and thereby improve the dynamic range of the system.

Another measure of dynamic range enhancement is provided by the focusing optics. The focusing optics includes first and second lenses maintained in fixed positions in the path of the beam and wavefront. An arrangement of optical elements is disposed between the lenses in the path of the beam and the wavefront. The optical elements are adjustable to change the optical path length between the lenses. If an optical correction is desired, the distortions are converted to an optical correction, which, if placed in the path of the wavefront, causes the wavefront to appear approximately as a plane wave. The optical correction can be in the form of a lens or an amount of corneal material ablated from the eye.

SUMMARY OF THE INVENTION

It is therefore an object of the present invention to provide a system and method for filtering sensor image wavefront data from an irradiated eye.

It is a further object to provide such a system and method applicable to Hartmann-Shack images.

It is another object to provide such a system and method for removing noise in the image data.

It is an additional object to provide such a system and method for removing speckle in the image.

It is also an object to provide such a system and method for filtering out nonuniform background noise.

It is yet a further object to provide such a system and method useful in analyzing highly aberrated eyes.

It is yet another object to provide a system and method for extending a range of a Hartmann-Shack-based wavefront sensor.

These and other objects are achieved by various embodiments of the present invention. A first aspect of the invention is for improving a quality of sensor image data from a wavefront emanating from an eye. The sensor image data comprise a pixel array of intensities. The method comprises the steps of populating a filter array with a coefficient at each position of the array and applying the filter array to each position in the pixel array. The system comprises a processor and a software package adapted to perform the above method steps.

A second aspect of the invention is for extending a range of a wavefront sensor for sensing a wavefront emanating from an eye. The method comprises the steps of focusing collimated light onto a lenslet array. An output of the lenslet array comprises a grid formed by edges of the lenslets and a reference spot in at least some members of the grid. Each reference spot has a known relationship to the grid member and a centroid. A position of each reference centroid and a relationship between the reference centroids are determined.

Next a wavefront emanating from an eye is focused onto the lenslet array. The output from the lenslet array comprises the grid and aberrated eye spots thereon, with each eye spot having a centroid. A position of each eye spot centroid and a relationship between the eye spot centroids are determined.

One known relationship between one reference centroid and the centroid of one eye spot is identified. Finally, at least some of the remaining relationships between the reference centroids and the eye spot centroids are determined. The determined relationships provide a measure indicative of the eye aberration.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–16C.

By way of illustrative example, the present invention will be described with respect to diagnosing and correcting a human eye. However, it is to be understood that the teachings of the present invention are applicable to any optical system having a real image focus that can be, or can be adapted to diffusely reflect a focused spot of radiation from a rear portion of the optical system back through the optical system as a wavefront of radiation. Thus the present invention can be used with human or animal eyes of patients that may be alive or dead, or any man-made optical system.

Correction of the human eye may be used in conjunction with or based upon the diagnostic information provided by embodiments of the present invention, including the use of lasers that photoablate corneal tissue through the use of broad beam excimer lasers such as are well known in the art.

A method of using wavefront analysis to determine an appropriate optical correction has been described in application Ser. No. 09/566,668, the disclosure of which is incorporated herein by reference. As described therein with reference to an ideal eye the ideal emmetropic or perfect eye diffusely reflects an impinging light beam from the back of its retina (i.e., the fovea centralis) through the eye's optics, which includes a lens and cornea. For such an ideal eye in a relaxed state, i.e., not accommodating to provide near-field focus, the reflected light exits the eye as a sequence of plane waves. However, a typical eye normally has aberrations that cause deformation or distortion of a reflected wave exiting the eye, where the aberrated eye diffusely reflects an impinging light beam from the back of its retina. For the aberrated eye, the reflected light exits the eye as a sequence of distorted wavefronts described mathematically as $W(x,y)$.

Figure 2:
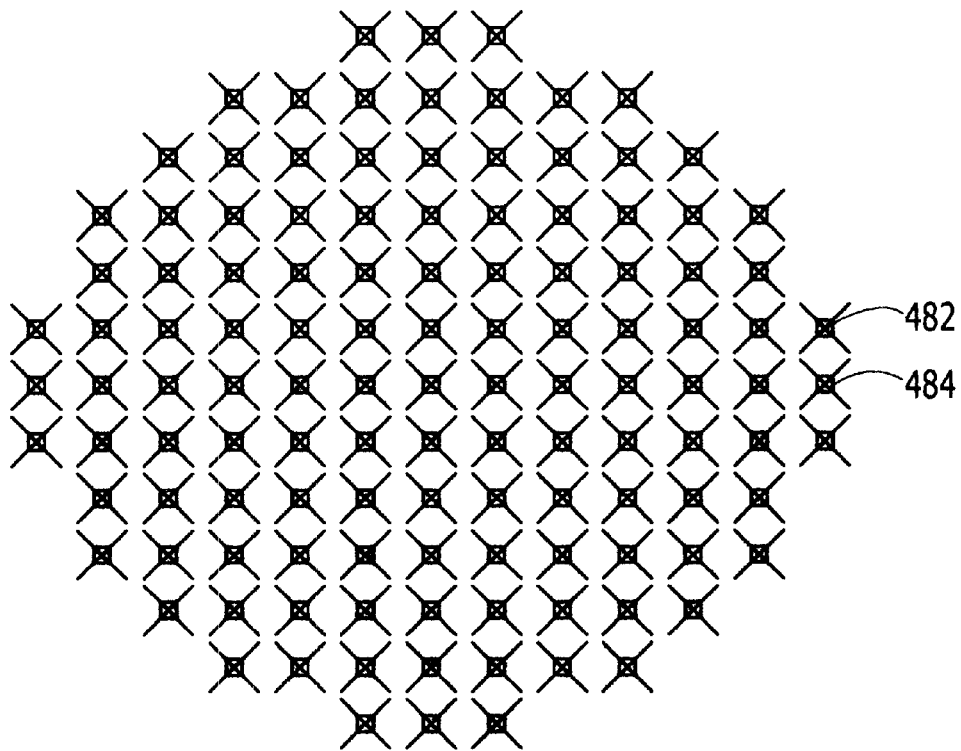
FIG. 2 illustrates a CCD image including centroids.
Figure 3:
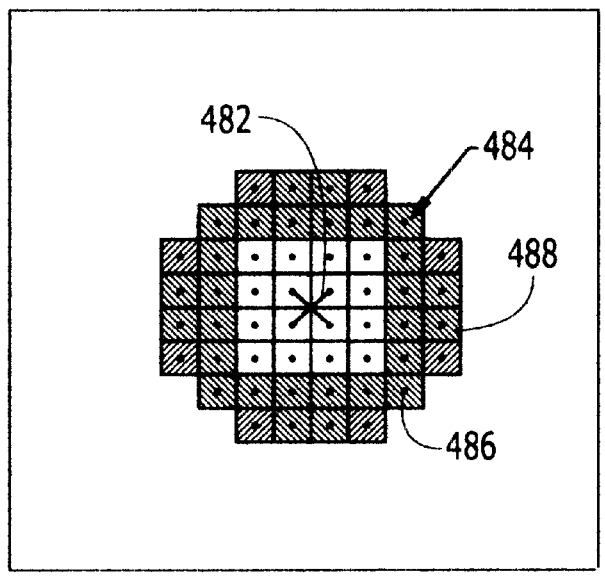
FIG. 3 is an enlarged image of a spot.
Figure 4:
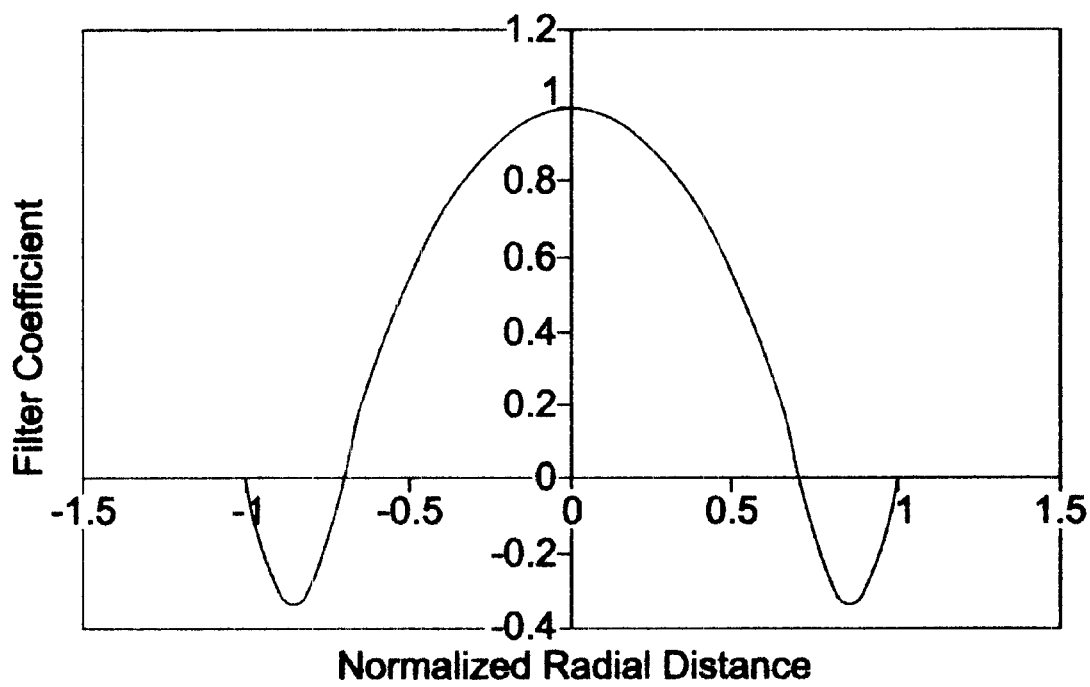
FIG. 4 illustrates a spatial filter operable in one embodiment of the present invention.

By way of example, a first aspect of the present invention will be discussed with reference to FIGS. 1–9. The system comprises a wavefront analyzer that comprises a two-dimensional array 33 of identical spherical lenslets 34, as illustrated with reference to FIG. 1. In such an embodiment, the lenslet array 33 may be operable by the positioning apparatus 42 such that separation distance F is independent of the focal length f that defines the focal plane of the lenslet array 33, which is represented by dashed line 35. Each wavefront portion 37 passing through a subaperture of the lenslet array 33 is reduced in size (e.g., diameter) but is not necessarily brought to a minimum focus at the planar array 36 as it would be if separation distance F were equal to focal length f. In the operation of this embodiment configuration, the lenslet array 33 is positioned to concentrate the light in each wavefront portion of an area for providing sufficient intensity onto the planar array 36, yet still illuminating a substantial plurality of cells 38 for greatest accuracy in determining the deflection of the centroids 482 (FIGS. 2 and 3).

Regardless of the structure of the wavefront sensor, the processor 40 computes each two-dimensional centroid 482 of each spot 484 generated by the wavefront 24. The amount of two-dimensional centroid shift relative to the centroid of the calibrating spot for each designated area associated with a corresponding subaperture of lenslet array 33 (see FIG. 10A) is divided by the separation distance F to generate a matrix of local slopes of the wavefront, i.e., $\partial W(x,y)/\partial x$ and $\partial W(x,y)/\partial y$ at the (x,y) coordinates of the centers of the corresponding subaperture of lenslet array 33. For simplicity of discussion, these will be indicated by $P(x,y)=\partial W(x,y)/\partial x$ and $Q(x,y)=\partial W(x,y)/\partial y$, respectively.

A method is herein described for identifying individual spots and correlating their geometry. The apparatus is configured such that the optical axis is aligned to the center of a particular aperture at the entrance face of the wavefront sensor. This aperture is located at or near the center of the entrance face. If the probe beam entering the eye is also aligned to the system optical axis, then due to the reversible nature of light rays, a light spot will always be seen directly behind the aligned aperture. That is, a spot 480 will always be seen on the CCD sensor 36 at this location (see FIG. 10A), regardless of the wavefront aberrations, and will always correspond to the overlying aperture. Immediately adjacent spots will be minimally displaced from their "zero-slope" locations. As one moves farther from the central reference spot 480, generally greater spot displacements will occur. Using this knowledge, it is a relatively straightforward process to identify all the spots in the CCD pattern and establish their geometric relationships.

The displacement of the centroid 482 from that 483 of a perfectly collimated light beam, corresponding to ideal and emmetropic vision, is then calculated and used to determine the wavefront slope at each sample location. The location of the centroids 483 for a collimated light beam may either be directly measured in a calibration step prior to the patient exam or taken from a calculated reference pattern based on the wavefront sensor construction.

Once a valid measurement of an eye has been made, the next step is to measure the local slopes of the wavefront. It is necessary for the software to compute the centroids 482 of the clusters of light on the CCD array 36 and then determine the distances of each of these centroids 482 from the corresponding reference centroids 483. The centroids are determined by first computing which pixels should be processed and grouping them together into clusters. The intensity-weighted centroid of each cluster is then computed. As illustrated with reference to FIG. 2, an example of an image from a myopic eye with the computed centroids 482 of cluster 484 marked by "X"s is shown. FIG. 3 illustrates a closeup of one of the clusters 484 and displays not only the centroid 482 but also the pixels 486 used in the centroiding calculation for the cluster 484. CCD pixels 488 processed in the centroiding algorithm are marked by dots. This algorithm, by way of example, isolates centroids 482 by use of a spatial filter that removes stray light signals that create noise for the CCD image. Such filtering may be desirable before calculation of light cluster positions.

Without filtering, computation of the cluster centroids 482 may be made difficult as a result of one or more potential problems: Noise on the image such that individual pixels with no actual data content may be brighter than pixels containing relevant data; speckle in the image may result in valid data clusters 484 having irregular profiles with significant variation in intensity of adjacent pixels; haze or background noise may be high relative to the actual data or may be nonuniform across the image; intensity of valid data may be nonuniform across the image; scatter from different parts of the eye may result in spurious signals on the image; and high levels of aberrations in the eye may significantly distort the clusters of valid data, by way of example.

Figure 9:
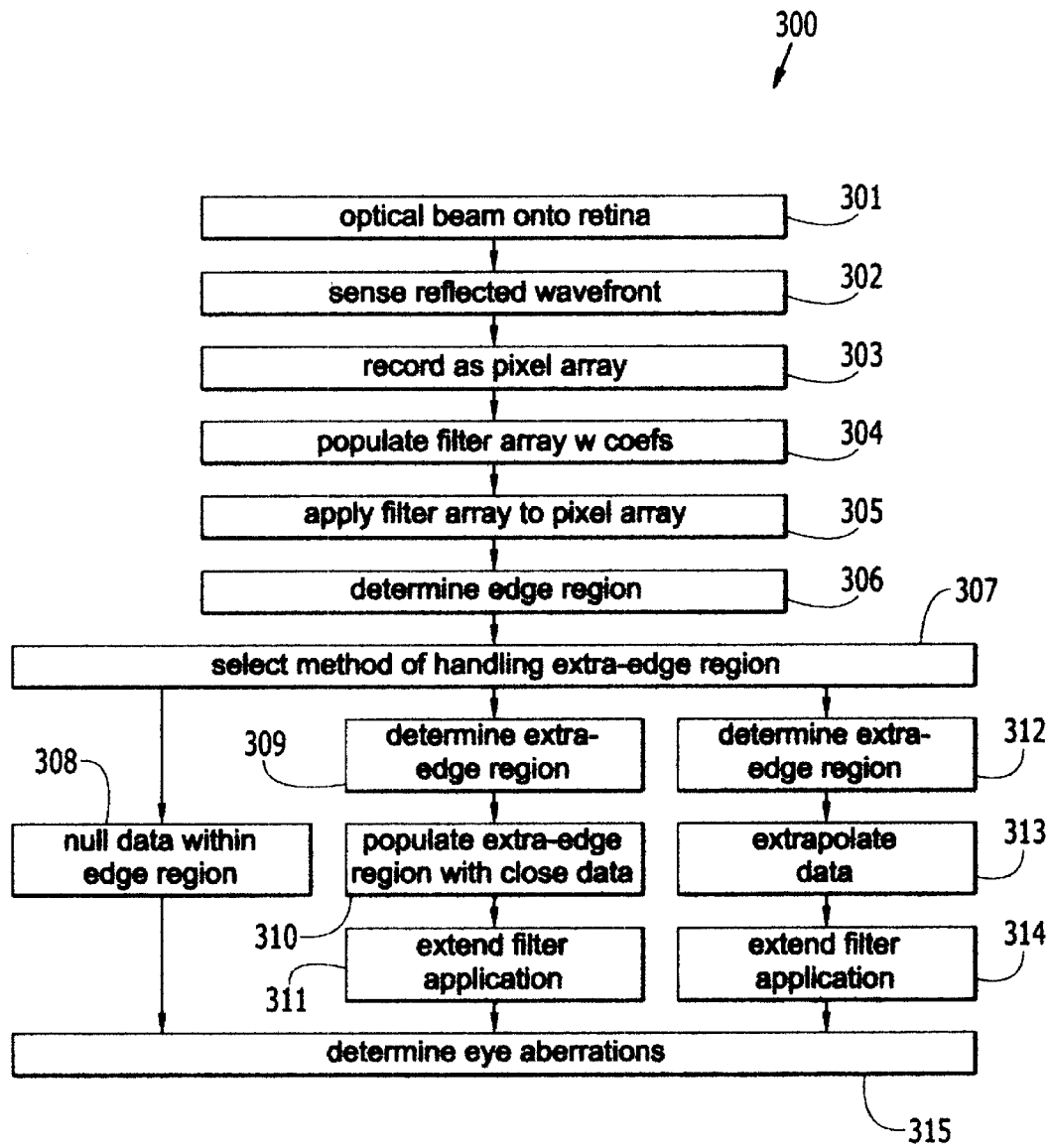
FIG. 9 is a flow chart of the application of the spatial filter to image data.

The creation and application of a spatial filter of the present invention is shown in flowchart form in FIG. 9. The spatial filter permits a recomputation of the brightness of each pixel in a bitmap using a weighted-averaging technique that considers surrounding pixels. In a particular application herein described for illustration and by way of example, the spatial filter is designed to: yield a maximum value when centered on valid data; reduce an effect of individual bright pixels or small groups thereof; normalize background levels; smooth valid data profiles; and simplify the task of extracting the valid data from background noise or haze.

Figure 1:
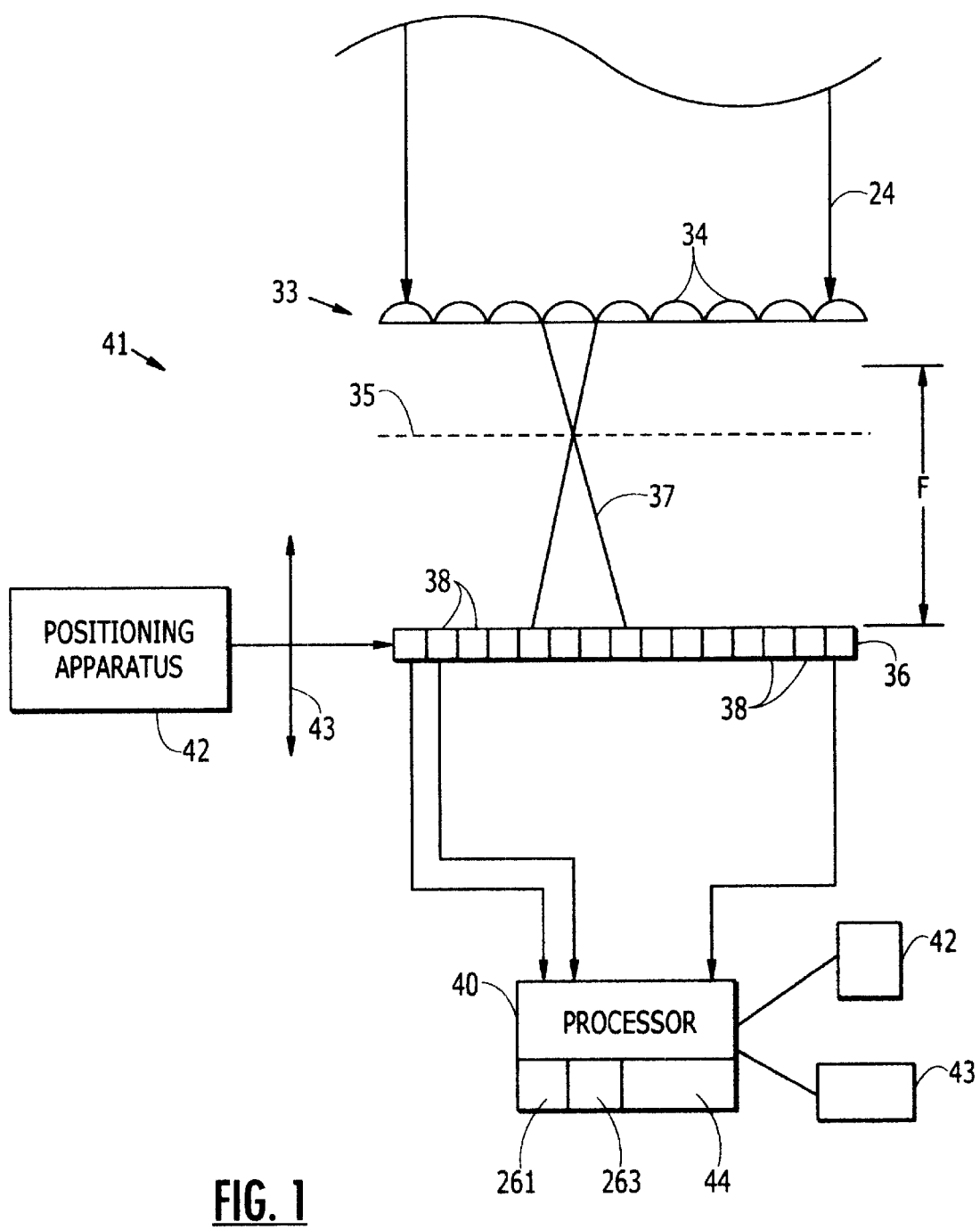
FIG. 1 is a schematic of a wavefront analyzer used in the present invention.

The spatial filter is embodied in a software package 261 resident on a processor 40, which in turn is part of the wavefront analyzer 41 (FIG. 1). Another software package 263 resident on the processor 40 determines aberrations in the eye based upon the filtered image data, as discussed in application Ser. No. 09/566,668.

A filter employed in one embodiment of the present invention is square (n×n) and includes real values (positive and negative) assigned to each pixel. The filter is designed to be optimally matched to images obtained from eyes with high, yet measurable, levels of aberration. By way of example, a cross-section through the filter is illustrated with reference to FIG. 4. An effect of applying such a filter improves an image 50 such as illustrated with reference to FIG. 5 to the image 50' illustrated in FIG. 6, by way of example, a cleaner image and one that is easily processed for identification and computation of cluster centroids 482. By applying the filter, images that would otherwise be deemed to noisy or of insufficient quality to process can now be processed and desired wavefront information computed.

Figure 7:
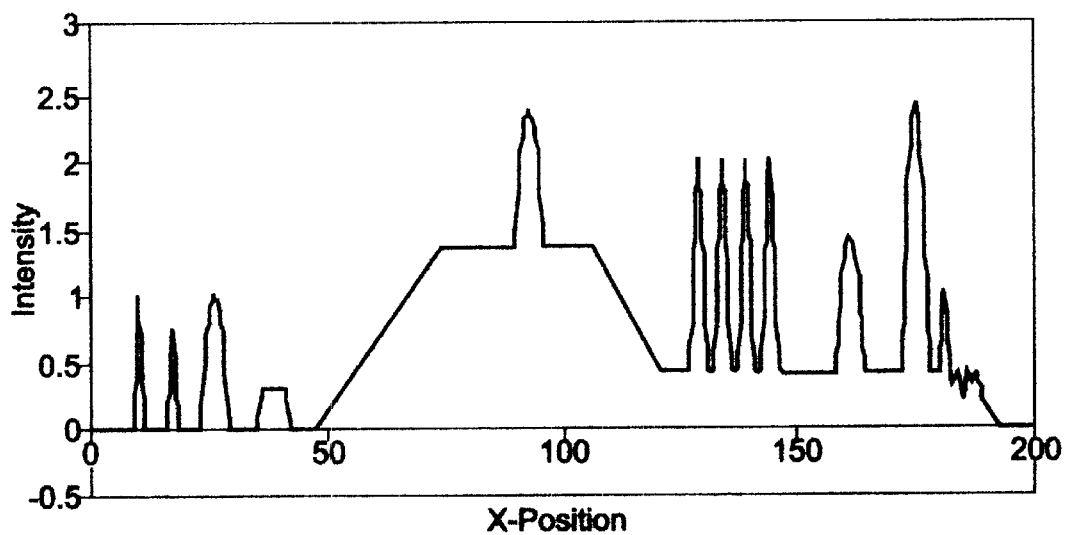
FIG. 7 is a two-dimensional sample of unfiltered data.
Figure 8:
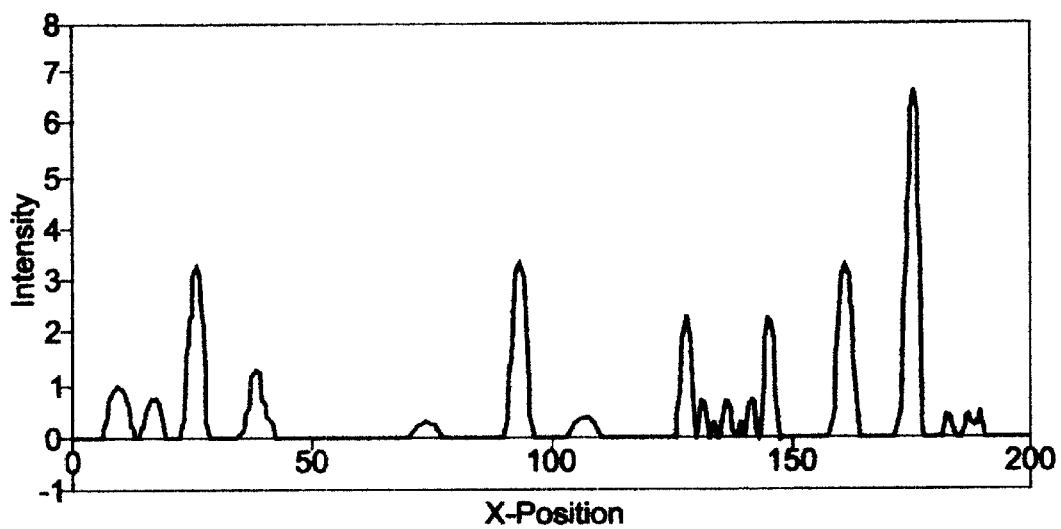
FIG. 8 illustrates the output of applying the spatial filter to the data of FIG. 7.

To illustrate the effect of applying this filter, a two-dimensional variant is applied to the image of FIG. 7 to yield the output of FIG. 8. An analysis of exemplary FIG. 7 yields several insights:

1. Valid data exist around locations 26, 93, 161, and 175 and are of an expected profile (i.e., the same profile as the filter).
2. Noise spikes of varying magnitude are present at 10, 17, 129, 134, 139, 144, and 181. (Note: those between 129 and 144 inclusive are wider and are not truly spikes.)
3. The background level varies across the plot.

It may be seen, therefore, that it is not possible to define a single threshold that would be exceeded by the valid data intensities and yet not by the noise and other unwanted data such as the high background levels in the middle of the plot. The result of applying a two-dimensional spatial filter (i.e., one similar to the profile shown in FIG. 4) to these data is shown in FIG. 8. Note that with a two-dimensional filter the coefficients at the edges have less effect than with a three-dimensional filter, and so the magnitudes of the coefficients need to be increased accordingly. In this particular case the negative values at the edges need to be more negative.

In FIG. 8 the highest values correspond to the valid data locations. The problem of varying background levels has been removed, and the use of a simple threshold can uniquely identify the locations of valid data.

Figure 5:
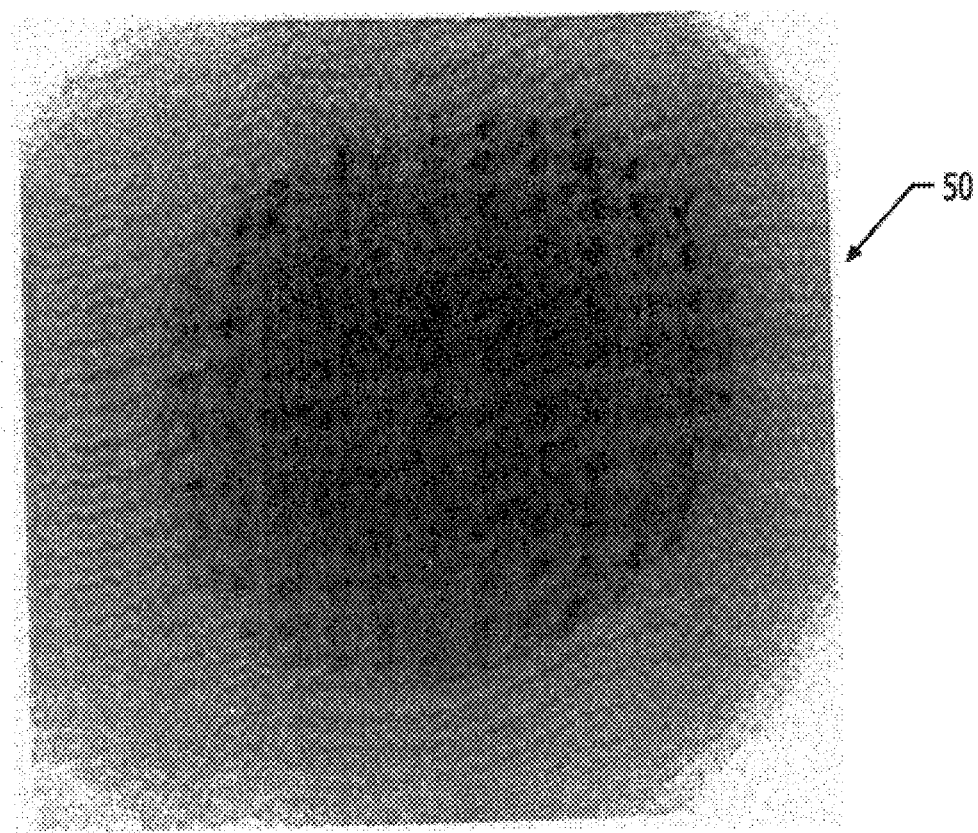
FIG. 5 illustrates a noisy CCD image before filtering to provide an image as illustrated with reference to FIG. 2.
Figure 6:
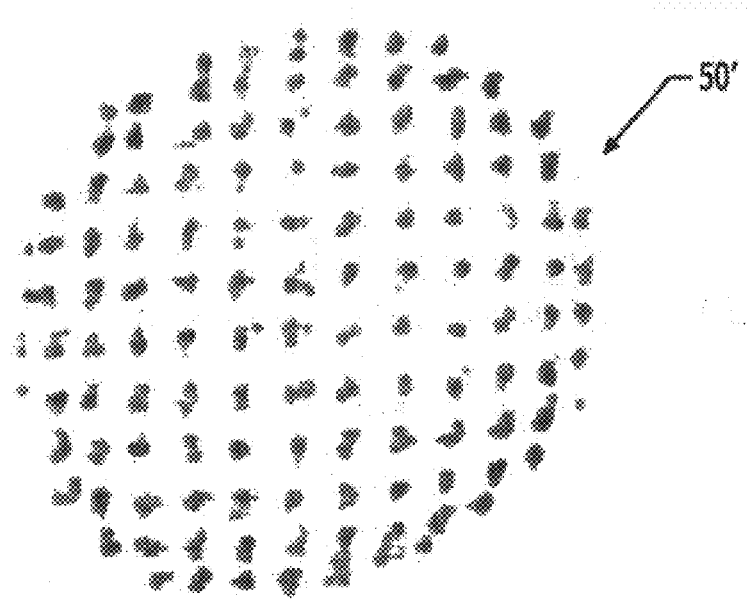
FIG. 6 is an exemplary Hartmann-Shack wavefront image after applying a spatial filter.

The three-dimensional filter (with coefficients at n×n x and y locations) works in a very similar matter to yield the intensities shown in FIG. 6 from those in FIG. 5.

The procedure 300 by which the spatial filter is applied will now be described with reference to FIG. 9:

1. Direct an optical beam onto the retina (block 301).
2. Sense the reflected wavefront (block 302).
3. Record the reflected wavefront as a pixel array (block 303).
4. The filter is created by populating an n×n array with the required coefficients (block 304). Note that a square array is used, but the coefficients are such that it is approximately radially symmetric.
5. The new intensities are computed at all locations (block 305) from a combination of the filter coefficients and the original intensities using the following exemplary iterative approach:

```
initialize new intensities to 0
for all x locations (Ix) to process in image
    for all y locations (Iy) to process in image
        for filter x offset (Fx) from -n/2 to +n/2
            for filter y offset (Fy) from -n/2 to +n/2
                newXaddress = Ix + Fx
                newYaddress = Iy + Fy
                    delta Intensity = filter coefficient(Fx,Fy) * Original Intensity
(newXaddress, newYaddress)
                new intensity(Ix,Iy) = new intensity(Ix,Iy) + delta intensity
            end
        end
    end
end
```

Note that the terminology "for all x locations (lx) to process an image." It is not possible to apply the spatial filter in the normal way when the target pixel is closer than n/2 pixels to an edge, since the algorithm would attempt to address nonexistent data.

6. Thus an edge region needs to be determined (block 306), and
7. A method selected to handle the extra-edge region (block 307).

There are a number of ways to address this:

a. Zero or null out all data within this edge region (block 308).
b. Determine the extra-edge region (block 309) and allow the filter to run all the way out to the edge and for data beyond the image assume that it is of the same intensity as the data closest to this location at the edge of the image (block 310), and extend the filter application (block 311).
c. Determine the extra-edge region (block 312) and extrapolate beyond the image (linearly or otherwise) to compute data (block 313), so that the filter may be used out to the edge of the image (block 314).

The most robust of these is to null the edge data (block 308).

Thus by applying filters of the kind described here, images that would otherwise be deemed too noisy or of insufficient quality to process can be process can be processed and the required wavefront information computed (block 315).

Figure 16A:
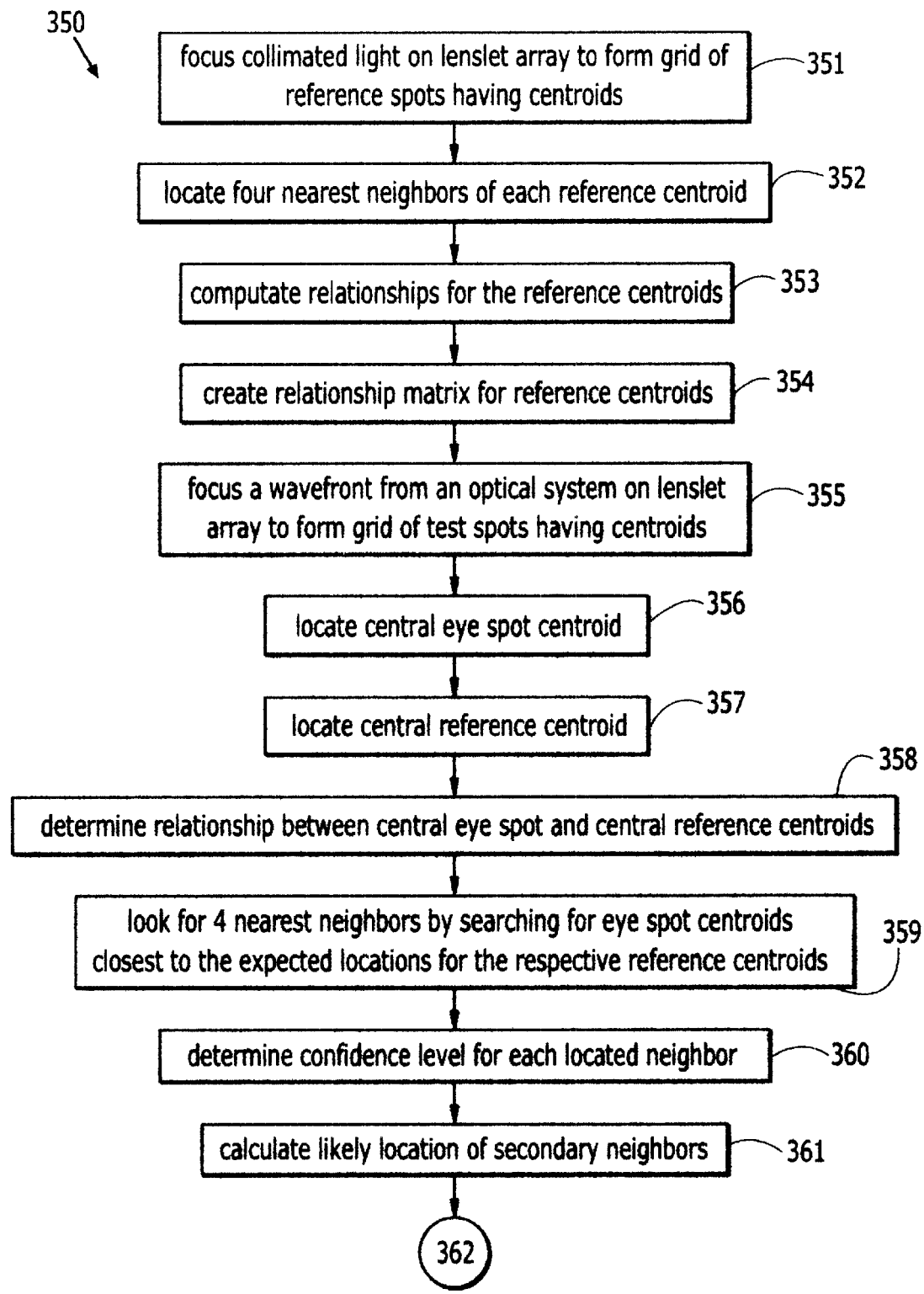
FIGS. 16A–16C is a flowchart of the method of the present invention.
Figure 16B:
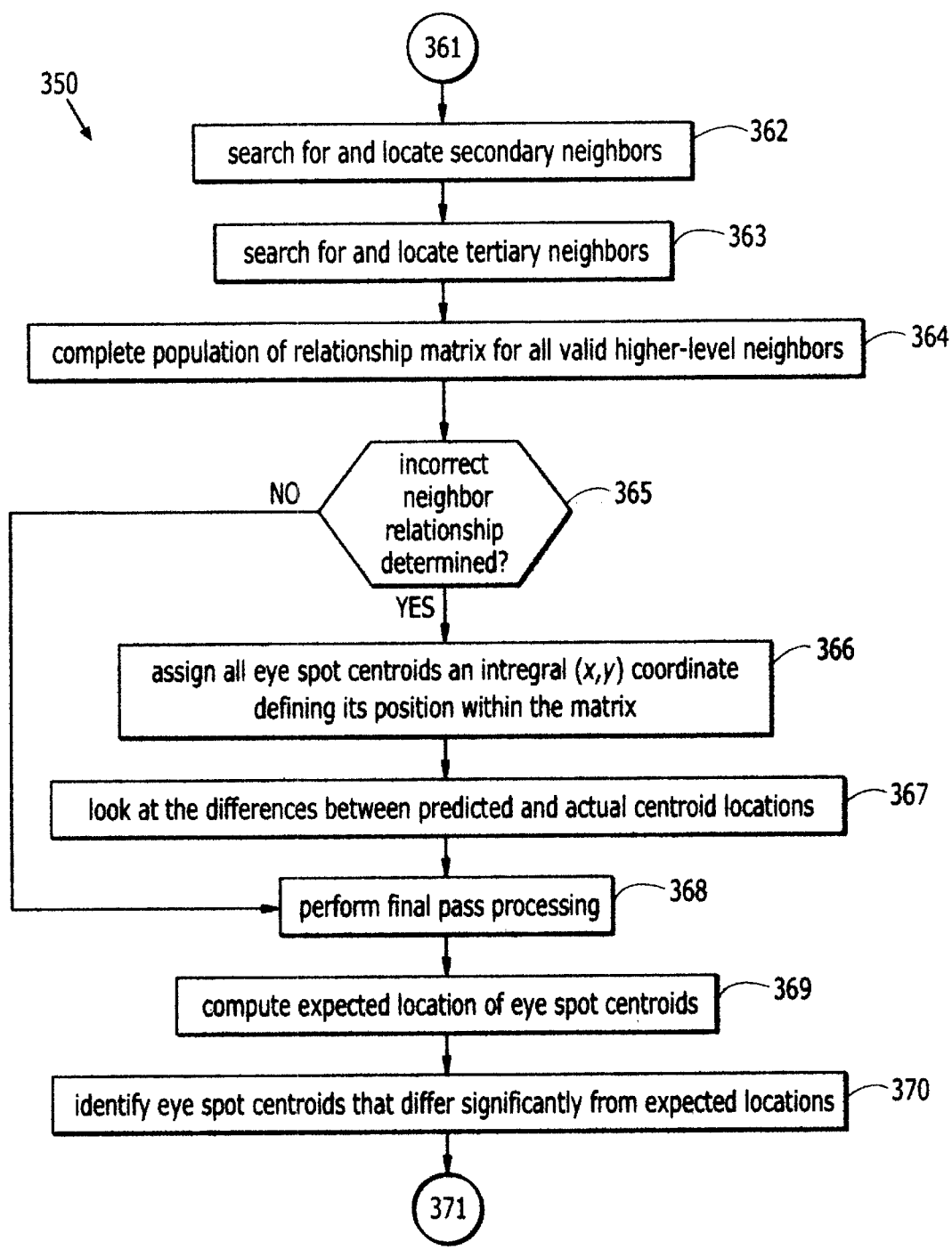
Figure 16C:
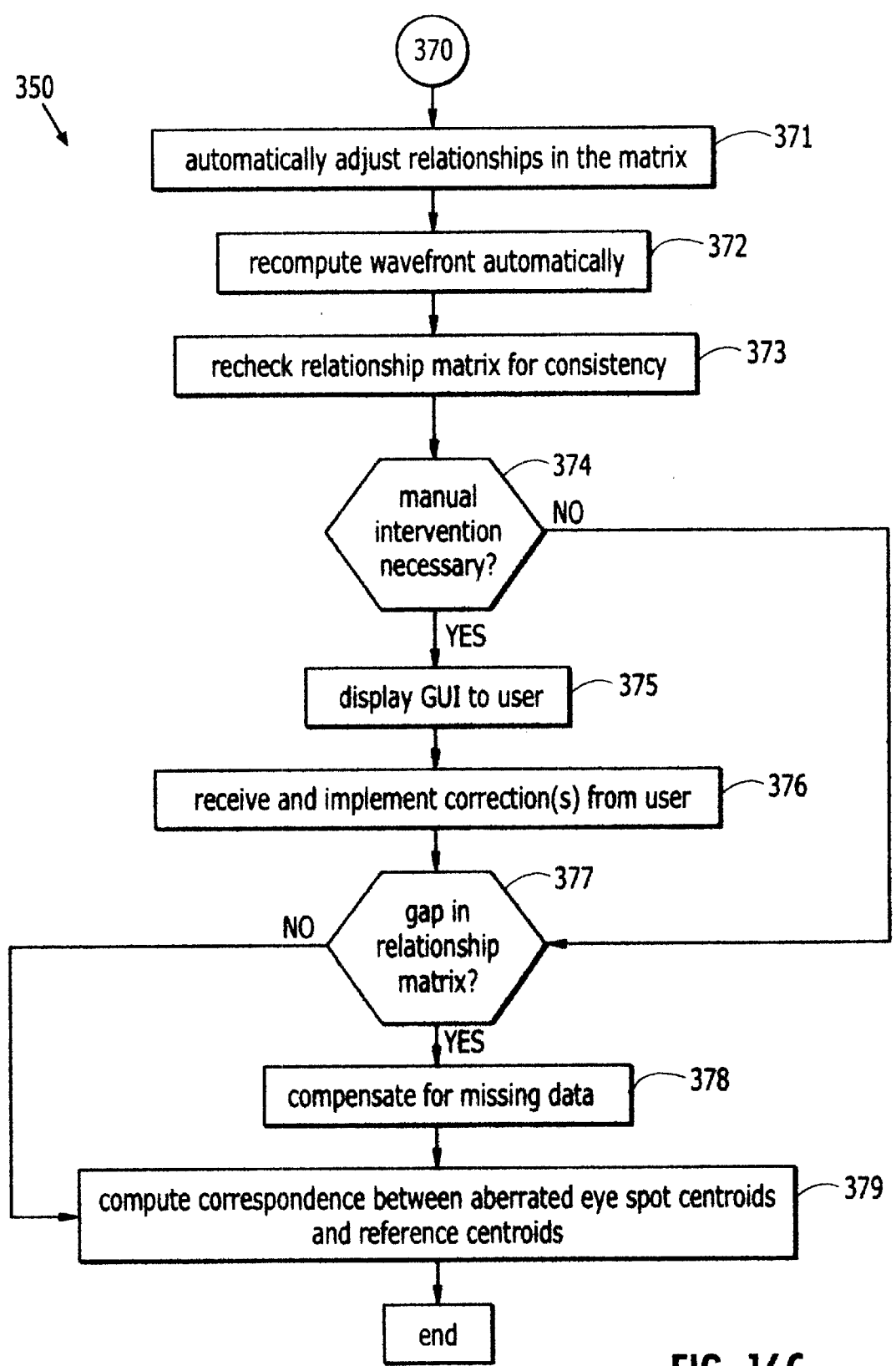

A second aspect of the present invention, which is for measuring eyes or other optical systems having relatively large levels of aberration, will now be discussed with reference to FIGS. 10A–16C, with FIGS. 16A–16C comprising a flowchart of the method 350 of the present invention, which is mediated by a software package 44 resident on the processor 40, which has routines for carrying out the steps of the invention (FIG. 1). If a collimated light source is focused by the lenslet array 33 (block 351), the spots fall in the respective centers of boxes 485 that form a grid 486 created by the projection of the lenslet borders, the spots comprising "reference spots" 481, with the centers of these spots comprising "reference centroids" 483 (filled circles, FIG. 10A). These "boxes" 485, which are members of the projected grid 486, are created in this embodiment because the lenslets 34 are square; it will be understood by one of skill in the art that alternate shapes will be created with differently shaped lenslets, and that a grid formed by other lenslets will comprise members having different shapes.

Figure 11:
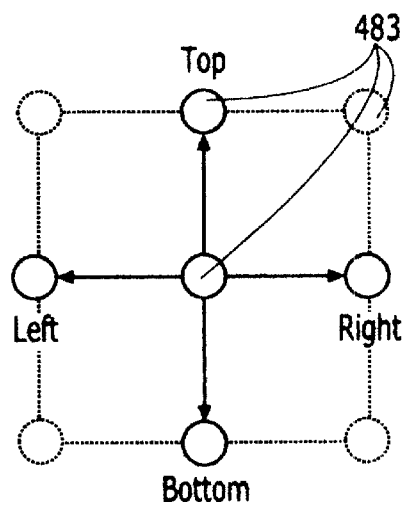
FIG. 11 illustrates relationships between a reference centroid and its nearest neighbors.

Relationships are then determined between the reference centroids 483 by locating, in the square array embodiment, the four nearest neighbors, that is, those above, below, and to either side of each reference centroid 483 not adjacent an edge of the grid 486 (block 352; FIG. 11). It will be obvious to one of skill in the art that for nonsquare lenslet patterns there may be relationships of interest other than these four.

Figure 12:
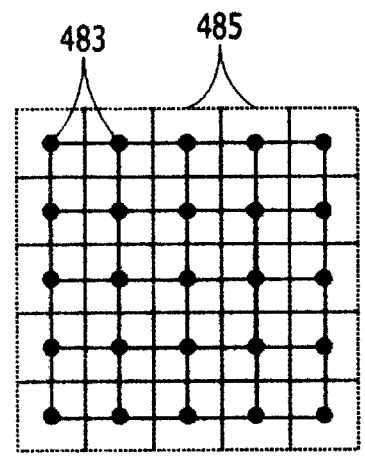
FIG. 12 is a schematic diagram of the relationships between all reference centroids and their nearest neighbors.

The computation of the relationships for the reference centroids 483 (block 353) is fairly straightforward because the reference centroids 483 always lie within their respective grid boxes 485. The computation results in the creation of a relationship matrix (block 354) such as shown in FIG. 12.

Figure 10A:
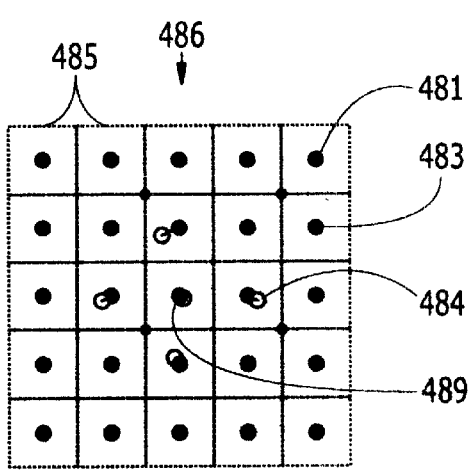
FIG. 10A is a schematic diagram of a grid of boxes populated by reference and eye spot centroids with a low level of aberration.
Figure 10B:
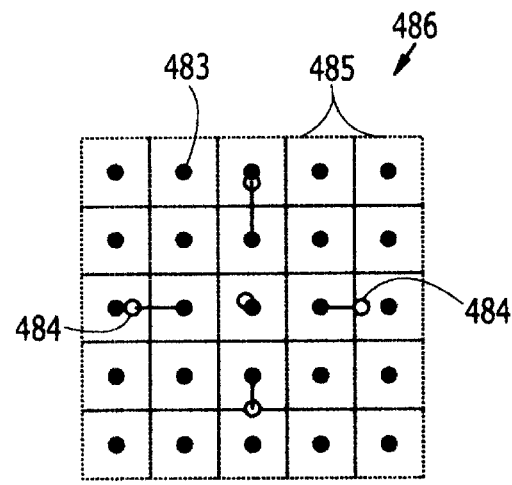
FIG. 10B is a schematic diagram of a grid of boxes populated by reference and eye spot centroids with a high level of aberration.

If the input light is not collimated, the spots are offset from the center of the boxes 485 by an amount proportional to the local slope in the wavefront at the location of the lenslet 34. The open circles in FIG. 10A show the location of the spots from the central five lenslets 34 (in a "plus" pattern) for an input wavefront that has only low levels of aberration. Here it is easy to discern which spot 484 from the aberrated wavefront corresponds to which reference spot 481 and, hence, which spot 484 corresponds to which lenslet 34. Correctly determining these relationships is an essential part of reconstructing wavefronts.

In eyes with larger levels of aberration, at least some of the spots 484 have fallen outside the boxes 485 in which their respective reference spots 481 reside (FIG. 10B; cf. FIG. 10A), hence making it more difficult to identify which spot 484 corresponds to which reference spot 481. If the approach used for determining the correct box 485 for FIG. 10A were followed, an incorrect wavefront calculation would result.

The present invention addresses this problem, with retention of both accuracy and range. It is believed that a key to being able to interpret the positions of centroids from highly aberrated eyes is the order in which relationships are determined. One approach would be to take each centroid from an aberrated wavefront and attempt to determine, centroid by centroid, the corresponding reference centroid. This may be done if the measurement system is configured so that the eye spot centroids always lie within the lenslet boundaries but is extremely difficult otherwise.

A wavefront measurement system can be configures such that the centroids always remain within the lenslet boundaries by positioning the sensor, typically a CCD, sufficiently close to the lenslet array 33. The disadvantage of this technique is that the system is less sensitive.

Another approach would be to simply limit the magnitude of the aberrations attempted to be measured with the system and declare any wavefronts with aberrations larger than this invalid.

These approaches are clearly not ideal; therefore, if it is desired to maintain both accuracy and range while measuring highly aberrated wavefronts, a different approach, that of the present invention, to determining the relationships is believed preferable to be used.

In a highly aberrated wavefront, not only can the locations of the eye spot centroids 482 (see FIG. 3 for a full view of an eye spot and its centroid) lie outside its respective grid box 485, but also the spacing between eye spot centroids 482 can vary significantly across the grid 486, and the relationship grid to be determined can have an irregular shape (cf FIG. 12).

Figure 13:
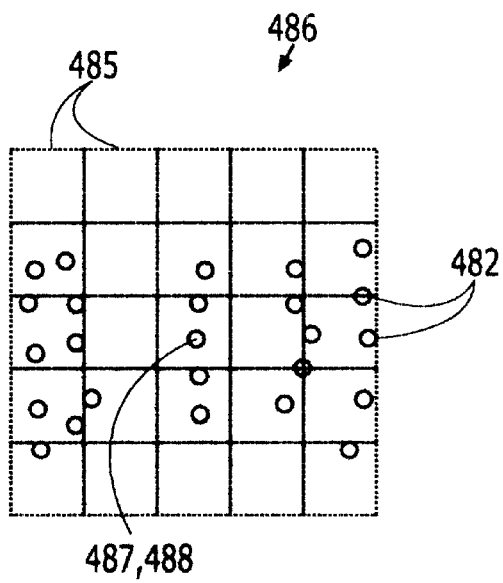
FIG. 13 is a schematic diagram of eye spot centroids obtained by a highly aberrated wavefront.
Figure 14:
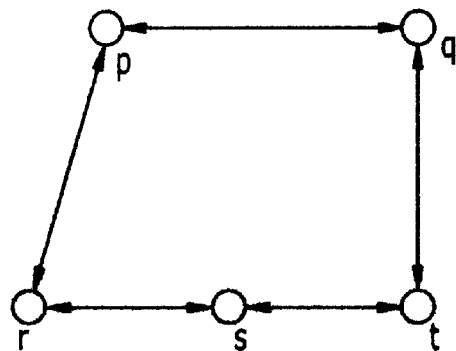
FIG. 14 illustrates an error in determining nearest neighbors.
Figure 15:
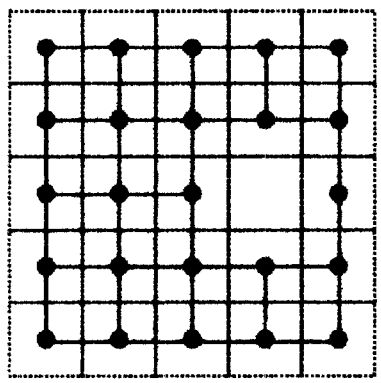
FIG. 15 illustrates an error caused by missing sensor data.

An example of the type of eye spot centroid pattern that can be obtained from a highly aberrated wavefront from an optical system such as an eye is shown in FIG. 13 (block 355). In this exemplary pattern there are 25 eye spot centroids 482 corresponding to the central 5×5 lenslets 34, but the spacing varies significantly across the pattern, and a more sophisticated approach is required in order to identify the nearest neighbors correctly.

In the exemplary apparatus of the present invention, which employs a Hartmann-Shack-based wavefront measurement system 41, correct alignment ensures that one eye spot 487 having centroid 488 is always located in the middle of the CCD sensor 36. Thus the method includes locating this central eye spot centroid 488 (block 356) and the central reference centroid 489 (FIG. 10A, block 357) and their relationship to each other (block 358), which serves as the starting point in populating the relationship matrix.

Beginning with the central eye spot centroid 488, look for its four nearest neighbors above, below, and to either side thereof. In order to locate the correct nearest neighbors, search for eye spot centroids 482 that are closest to the expected locations by using the expected locations for the respective reference centroids 483 (block 359).

Next a determination is made as to whether or not there are valid neighbors in each direction by computing the eye spot centroids 482 considered most likely to be neighbors and then determining a confidence level (block 360). The confidence level includes a distance and an angle of each neighbor from its respective expected neighbor location.

Based upon the actual location of the neighbors that are found, a likely location of the neighbors for these, the secondary neighbors, is then calculated (block 361). As an example, if a neighbor was located 80% of the expected distance from the central eye spot centroid 488, then it is deemed likely that its neighbor in the same direction will also be closer than would be expected for a collimated wavefront (reference centroid). This computation accounts for changes in distance and angle to neighbors and also addresses rates of change of distances, such as if eye spot centroids 482 are moving closer together as the periphery is approached.

For all new, valid (secondary) neighbors located (block 362), repeat the search for tertiary neighbors in all directions where there are currently no neighbors for which data populate the matrix (block 363). For example, for the eye spot centroid 482 determined to be to the right of the central eye spot centroid 488, there is no need to look for a left-hand neighbor, since that relationship has already been established.

Finally, continue finding all higher-level neighbors and populate the relationship matrix until no more valid neighbors can be identified (block 364).

Some problems may occur in the neighbor identification process. For example, noise in the detected data may cause an incorrect classification of a spurious signal as a valid neighbor. It is also possible to determine an invalid set of neighbors (block 365), such as those that are not physically possible. Note, for example, FIG. 14, wherein if q is p's right-hand neighbor and t's upper neighbor, then if r is p's bottom neighbor, it may be computed that t must be r's right-hand neighbor. As this is not the case, there is an error. One possible explanation is that eye spot centroid s is actually not a valid eye spot centroid 482, but a noisy or spurious signal. Another explanation is that all eye spot centroids 482 are valid, but that one or more of the computer neighbor relationships are invalid. Such conflicts should be resolved by the software algorithms.

The identification of possible conflicts is accomplished by assigning all eye spot centroids 482 an integral (x,y) coordinate that defines its position within the matrix (block 366). The central eye spot centroid 488 is (0,0); the one to the right is (1,0); the one above is (1,1), and so on. If, in FIG. 14, centroid r had coordinate (n,m), then following path r→p→q, it would be computed that q had coordinate (n+1, m+1). However, following path r→s→t→q, it would be computed that eye spot centroid q had coordinate (n+2, m+1). This conflict is automatically identified by the software, which then attempts to resolve it.

Resolution of the conflict is performed by looking at all eye spot centroids 482 close to the conflict and attempting to determine which neighbor relationships are most likely to be correct. This is done by looking at the differences between predicted and actual centroid locations (block 367). Referring again to FIG. 14, consider the case in which the neighbors of the centroid r are being computed, and it is determined that s is r's right-hand neighbor. Upon computing this "proposed neighbor," the system checks for possible conflicts and identifies that t has already claimed s as its left-hand neighbor. The system then determines a confidence level for centroid r's claim of s as its neighbor based upon the angle and distance of s from where r had expected to find its right-hand neighbor. A similar confidence level is calculated for t. The centroid having the higher confidence level is selected as the neighbor of s, and any prior connections that had been established on the basis of the lower-confidence-level centroid are declared invalid and are broken, and the higher-confidence-level connection is recorded.

Automatic conflict resolution cannot be performed with 100% accuracy, but should be correct a majority of the time. Manual intervention to allow for corrections in the small number of cases in which problems persist is provided (block 374).

In order to minimize the need for manual intervention (block 374), final pass processing can be performed automatically (block 368). If a small number of errors have occurred in the relationship matrix generation, then the impact on the reconstructed wavefront is small. If a computation is made, based upon the reconstructed wavefront, of an expected location of the eye spot centroids (block 369), it is possible to identify eye spot centroids that differ significantly from these expected locations (block 370). If there were no errors in the relationship matrix, then the errors are small for all eye spot centroids in the matrix. If there were a small number of errors, then the identification of these errors allows for some automated adjustment of the relationships in the matrix such that these errors are minimized (block 371). The wavefront can then be automatically recomputed (block 372) and the relationship matrix rechecked for consistency (block 373).

Manual intervention in a preferred embodiment is provided via a graphical user interface (block 375) displayed on a display device 42 in electronic communication with the processor 40. As stated above, possible errors include a determination that a spurious or noisy signal represents a valid eye spot centroid and the computation of an incorrect neighbor relationship. The software 44 permits a user to correct such errors by using an input device 43 such as a keyboard or pointing device such as a mouse to perform corrections (block 376) such as:

1. Declare an eye spot centroid 482 as "not valid" so that it is excluded from the relationship matrix.
2. Define a centroid-to-centroid neighbor relationship.
3. Break a computed centroid-to-centroid neighbor relationship.

These capabilities allow the user to take images of extremely poor quality (e.g., having a low signal-to-noise ratio) and "clean them up" so that valid wavefronts can be computed.

Another potential problem is the presence of a gap in the relationship matrix (block 377). This may occur because of optical characteristics in the eye being examined. The software 44 can handle this problem (block 378) without permitting the missing data to corrupt the analysis of the reconstructed wavefronts.

To achieve this, the software 44 ignores the missing data; however, since there are so many data points available, the absence of these data does not significantly affect the results. Although fewer data points are available for the Zernike coefficient computations, there are typically hundreds of data points available. The number of polynomials being fitted (typically 14, and usually fewer than 44) is so much smaller than the number of data points, that one of skill in the art will recognize that a few missing data points will have negligible impact.

Once the relationships between all eye spot centroids 483, 482 from the reference and aberrated wavefronts have been computed, knowing the relationship therebetween permits the computation of the correspondence between aberrated eye spot centroids 482 and reference centroids 483 (block 379).

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are byway of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for measuring aberration in an eye comprising the steps of:

focusing collimated light onto a lenslet array, an output thereof comprising a grid formed by edges of the lenslets and a reference spot in at least some members of the grid, each reference spot having a known relationship to the grid member and a centroid;

determining a position of each reference centroid and a relationship between the reference centroids;

focusing a wavefront emanating from an eye onto the lenslet array, the output from the lenslet array comprising the grid and aberrated eye spots thereon, each eye spot having a centroid;

determining a position of each eye spot centroid and a relationship between the eye spot centroids;

identifying one known relationship between one reference centroid and the centroid of one eye spot; and determining at least some of the remaining relationships between the reference centroids and the eye spot centroids, the determined relationships providing a measure indicative of the eye aberration.

2. The method recited in claim 1, wherein the lenslet array comprises a square n×n array, the lenslets comprise substantially square lenslets, and each grid member comprises a substantially square box.

3. The method recited in claim 1, wherein each reference centroid is positioned within its respective grid member.

4. The method recited in claim 3, wherein each reference centroid lies substantially in a center of its respective grid member.

5. The method recited in claim 3, wherein the step of determining a relationship between the reference centroids comprises creating a matrix defining neighbors of each reference centroid.

6. The method recited in claim 5, wherein the matrix-creating step comprises defining four nearest neighbors of each reference centroid.

7. The method recited in claim 6, wherein the four nearest neighbors for each reference centroid not positioned adjacent a grid edge comprise reference centroids above, below, and one to each side of each reference centroid.

8. The method recited in claim 1, wherein one eye spot lies substantially in a center of the grid, and wherein the one known relationship determining step comprises determining a relationship between the grid-center eye spot centroid and its respective reference spot centroid.

9. The method recited in claim 8, wherein the remaining relationship determining step comprises searching for four nearest neighbors of the grid-center eye spot.

10. The method recited in claim 9, wherein the searching step comprises beginning a search at a center of each nearest-neighbor grid member.

11. The method recited in claim 9, wherein the remaining relationship determining step comprises calculating a distance and an angle of each of the nearest neighbors from the grid-center eye spot to compute a confidence level.

12. The method recited in claim 11, wherein the remaining relationship determining step further comprises searching for a secondary nearest neighbor of a selected one of the nearest neighbors based upon the distance and angle of the selected nearest neighbor.

13. The method recited in claim 12, further comprising the step of searching for remaining tertiary nearest neighbors of the secondary nearest neighbor.

14. The method recited in claim 13, further comprising the step of creating a matrix defining determined locations of eye spot centroids.

15. The method recited in claim 14, further comprising the step of searching for all remaining nearest neighbors until the eye spot centroid matrix is completely populated.

16. The method recited in claim 1, wherein the determining steps comprise automatically determining the relationship between reference centroids and between eye spot centroids and at least some of the remaining relationships between the reference centroids and the eye spot centroids under processor and software control, the software comprising means for identifying possible invalid determinations, means for displaying the determinations to a user, and means for receiving user input to alter at least one of the determined remaining relationships.

17. A method for measuring aberration in an optical system comprising the steps of:

providing a calibration matrix containing a two-dimensional position of a reference centroid and a positional relationship between the reference centroids;

focusing a wavefront emanating from an optical system onto a lenslet array, the output from the lenslet array comprising a test matrix containing a two-dimensional position of optical system spot centroids;

calculating a positional relationship between the optical system spot centroids and populating the test matrix with the calculated positional relationships;

identifying one known relationship between one reference centroid and the centroid of one eye spot; and determining at least some of the remaining relationships between the reference centroids and the eye spot centroids, the determined relationships providing a measure indicative of the eye aberration.

18. The method recited in claim 17, wherein the lenslet array comprises a square array and the calibration matrix comprises a pointer to four nearest neighbors of each reference centroid.

19. The method recited in claim 18, wherein the four nearest neighbors for each reference centroid not positioned adjacent a grid edge comprise reference centroids above, below, and one to each side of each reference centroid.

20. The method recited in claim 17, wherein the one optical system spot emanates substantially from a center of the lenslet array, and wherein the one known-relationship determining step comprises determining a relationship between the center optical system spot centroid and its respective reference spot centroid.

21. The method recited in claim 20, wherein the remaining relationship determining step comprises searching for four nearest neighbors of the center optical system spot.

22. The method recited in claim 21, wherein the remaining relationship determining step comprises calculating a distance and an angle of each of the nearest neighbors from the center optical system spot to compute a confidence level.

23. The method recited in claim 22, wherein the remaining relationship determining step further comprises searching for a secondary nearest neighbor of a selected one of the nearest neighbors based upon the distance and angle of the selected nearest neighbor.

24. The method recited in claim 23, further comprising the step of searching for remaining tertiary nearest neighbors of the secondary nearest neighbor.

25. The method recited in claim 24, further comprising the step of searching for all remaining nearest neighbors until the test matrix is completely populated.

26. The method recited in claim 17, wherein the calculating step comprises automatically calculating the relationship between optical system spot centroids and the determining step comprises automatically determining at least some of the remaining relationships between the reference centroids and the eye spot centroids, the automatically calculating and automatically determining steps under processor and software control, the software comprising means for identifying possible invalid determinations, means for displaying the determinations to a user, and means for receiving user input to alter at least one of the determined remaining relationships.

27. A system for measuring aberration in an eye comprising:
   a lenslet array positioned to receive a wavefront, an output thereof upon receiving collimated light comprising a grid formed by edges of the lenslets and a reference spot having a centroid in at least some members of the grid, each reference spot having a known relationship to the grid member and a centroid, an output thereof upon receiving an aberrated wavefront comprising the grid and an eye spot having a centroid in at least some members of the grid;
   a sensor for receiving the lenslet array output;
   a processor in data-receiving communication with the sensor; and
   software means resident on the processor for:
      determining a position of each reference centroid and each eye spot centroid and a relationship between the reference centroids and between the eye spot centroids;
      identifying one known relationship between one reference centroid and one eye spot centroid; and
      determining at least some of the remaining relationships between the reference centroids and the eye spot centroids, the determined relationships providing a measure indicative of the eye aberration.

28. The system recited in claim 27, wherein the lenslet array comprises a square n×n array, the lenslets comprise substantially square lenslets, and each grid member comprises a substantially square box.

29. The system recited in claim 27, wherein each reference centroid is positioned within its respective grid member.

30. The system recited in claim 29, wherein each reference centroid lies substantially in a center of its respective grid member.

31. The system recited in claim 29, wherein the software means, when determining a relationship between the reference centroids, creates a matrix defining-neighbors of each reference centroid.

32. The system recited in claim 31, wherein the matrix creation comprises defining four nearest neighbors of each reference centroid.

33. The system recited in claim 32, wherein the four nearest neighbors for each reference centroid not positioned adjacent a grid edge comprise reference centroids above, below, and one to each side of each reference centroid.

34. The system recited in claim 27, wherein one eye spot lies substantially in a center of the grid, and wherein the software means determines one known relationship by determining a relationship between the grid-center eye spot centroid and its respective reference spot centroid.

35. The system recited in claim 34, wherein software means determining the remaining relationship by searching for four nearest neighbors of the grid-center eye spot.

36. The system recited in claim 35, wherein the software means begins the search at a center of each nearest-neighbor grid member.

37. The system recited in claim 35, wherein the software means determines the remaining relationships by calculating a distance and an angle of each of the nearest neighbors from the grid-center eye spot to compute a confidence level.

38. The system recited in claim 37, wherein the software determines the remaining relationships further by searching for a secondary nearest neighbor of a selected one of the nearest neighbors based upon the distance and angle of the selected nearest neighbor.

39. The system recited in claim 38, wherein the software means searches for remaining tertiary nearest neighbors of the secondary nearest neighbor.

40. The system recited in claim 39, wherein the software means is further for creating a matrix defining determined locations of eye spot centroids.

41. The system recited in claim 40, wherein the software means is further for searching for all remaining nearest neighbors until the eye spot centroid matrix is completely populated.

42. The system recited in claim 27, wherein the software means is further for identifying possible invalid determinations, and the system further comprises a display in electronic communication with the processor for displaying the determinations to a user, and an input in electronic communication with the processor for receiving user input to alter at least one of the determined remaining relationships.

43. A software package for calculating aberration from data collected from an optical system comprising:
   a routine for reading a predetermined calibration matrix from a storage unit, the calibration matrix containing a two-dimensional position of a reference centroid and a positional relationship between the reference centroids;
   a routine for transforming output from a lenslet array, the output from an aberrated optical system, into a test matrix containing a two-dimensional position of optical system spot centroids;
   a routine for calculating a positional relationship between the optical system spot centroids and for populating the test matrix with the calculated positional relationships;
   a routine for identifying one known relationship between one reference centroid and the centroid of one eye spot; and
   a routine for determining at least some of the remaining relationships between the reference centroids and the eye spot centroids, the determined relationships providing a measure indicative of the eye aberration.

44. The system recited in claim 43, wherein the output comprises output from a substantially square lenslet array and the calibration matrix comprises a pointer to four nearest neighbors of each reference centroid.

45. The system recited in claim 44, wherein the four nearest neighbors for each reference centroid not positioned adjacent a grid edge comprise reference centroids above, below, and one to each side of each reference centroid.

46. The system recited in claim 45, wherein the one optical system spot emanates substantially from a center of the lenslet array, and wherein the one known relationship determining routine determines a relationship between the center optical system spot centroid and its respective reference spot centroid.

47. The system recited in claim 46, wherein the routine for determining the remaining relationships searches for four nearest neighbors of the center optical system spot.

48. The system recited in claim 47, wherein the routine for determining the remaining relationships also calculates a distance and an angle of each of the nearest neighbors from the center optical system spot and computes a confidence level for the nearest neighbors.

49. The system recited in claim 48, wherein the routine for determining the remaining relationships further searches for a secondary nearest neighbor of a selected one of the nearest neighbors based upon the distance and angle of the selected nearest neighbor.

50. The system recited in claim 49, wherein the software further searches for remaining tertiary nearest neighbors of the secondary nearest neighbor.

51. The system recited in claim 50, wherein the software further searches for all remaining nearest neighbors until the test matrix is completely populated.

52. The system recited in claim 43, wherein the software further comprises a routine for identifying possible invalid determinations, for directing a display of the determinations to a user, and for receiving user input to alter at least one of the determined remaining relationships.

* * * * *